Figure 1:
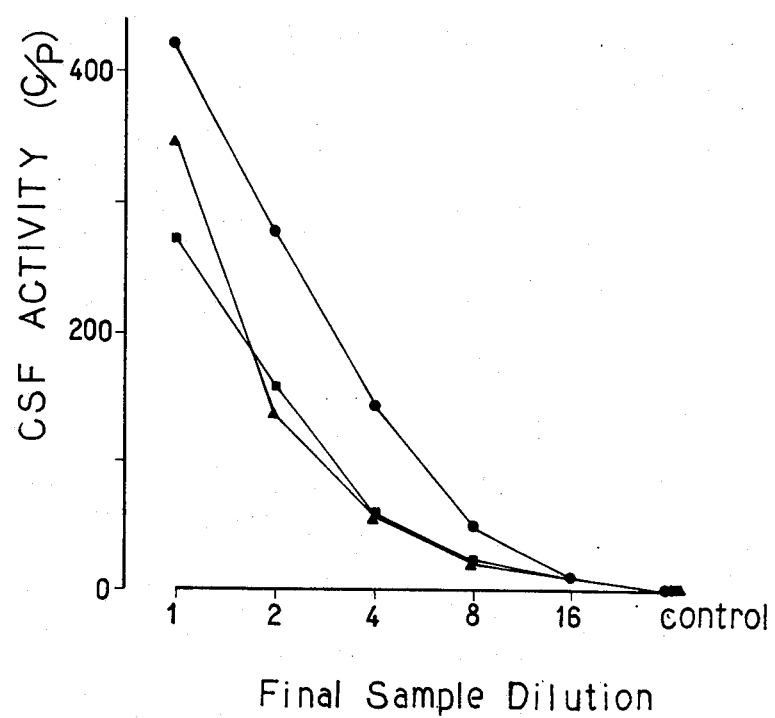

United States Patent [19]

Yamamura et al.

[11] Patent Number: 4,675,291
[45] Date of Patent: Jun. 23, 1987

[54] HUMAN CULTURED CELL LINE

[75] Inventors: Yuichi Yamamura, Takarazuka; Tadamitsu Kishimoto, Tondabayashi; Satoru Nakai; Yoshikatsu Hirai, both of Tokushima, all of Japan

[73] Assignee: Otsuka Pharmaceutical Co., Ltd., Japan

[21] Appl. No.: 586,558

[22] Filed: Mar. 6, 1984

[30] Foreign Application Priority Data

Mar. 15, 1983 [JP] Japan .................................. 58-43992

[51] Int. Cl.⁴ ........................ C12P 21/00; C12N 5/00; C12N 5/02
[52] U.S. Cl. ..................................... 435/68; 435/240; 435/241
[58] Field of Search ...................... 435/240, 68, 172.1, 435/241; 935/99–101; 530/351

[56] References Cited

U.S. PATENT DOCUMENTS 4,438,038  3/1984  Golde et al. ........................... 424/85
4,544,632  10/1985  Yamamura et al. .................. 435/68

OTHER PUBLICATIONS

Okada et al., Proc. Natl. Acad. Sci., vol. 78, pp. 7717–7721, 1981.
Irigoyen et al., J. Exp. Med., vol. 154, Dec. 1981, 1827–1837.
Lusis et al., Blood, vol. 57, No. 1 (Jan.), 1981.

Primary Examiner—Blondel Hazel
Attorney, Agent, or Firm—Larson and Taylor

[57] ABSTRACT

This invention provides a novel cultured cell line which is derived from human T leukemic cells and which produces a colony-stimulating factor (CSF). This invention also provides a process for preparing such human cultured cell line, and a process of producing a CSF from such cell line.

4 Claims, 18 Drawing Figures

HUMAN CULTURED CELL LINE

This invention relates to a novel human cultured cell line, and more particularly to a cultured cell line which is derived from human T leukemic cells, produces a colony-stimulating factor (CSF) and can be cultured permanently.

CSF is known as a body fluid factor which acts on granulocytic and macrophagic stem cells derived from bone marrow stem cells to grow them into matured hemopoietic cells, i.e., granulocytes and/or macrophages (Journal of Immunological Methods, 42, 253-284 (1981) and "Ketsueki no Byotaiseikagaku (Pathologic Biochemistry of Blood)", pp. 1-3, June 25, 1979, Asakura Shoten Co., Ltd.).

Because of its activity, CSF is useful for preventing and treating granulocytopenia and macrophagocytopenia in patients under cancer therapy, for preventing and treating various infections and also for treating patients with implanted bone marrow.

We have conducted extensive research to investigate into cell lines having sustained ability to produce human CSFs. In the course of the research, we found that the supernatant of cultures of the human T cell line CDM-AG ® (Proc. Natl. Acad. Sci., U.S.A., vol. 78, No.12, pp. 7717-7721 (1981)), already established by Yamamura and Kishimoto, present inventors, sometimes exhibits CSF activity. Through repeated selective incubation (cloning) thereafter conducted with the CSF activity as a target, we have succeeded in isolating cells having ability to produce a CSF and established them as a cultured cell line. We have found that the cell line can be maintained in vitro continuously with good stability and that the CSF can be produced in large quantities by incubating the cell line. These findings have matured to the present invention.

More specifically the present invention provides a human cultured cell line "AGR-ON" derived from human T leukemic cells and having the following characteristics:

(a) Form: The cell "AGR-ON" resembles lymphoid cell.

(b) Proliferation: The cell proliferates satisfactorily in RPMI-1640 culture medium containing 100 μM 8-azaguanine (8-AG), 10% fetal calf serum (FCS), $5 \times 10^{-5}$M 2-mercaptoethanol, 100 μg/ml streptomycin, 100 units/ml penicillin G, 50 μg/ml gentamycin and 1 mM glutamine.

(c) Subculture: The cell line can be subcultured continuously and indefinitely.

(d) Preservation in frozen form: The cell line can be preserved easily in liquid nitrogen for a prolonged period of time.

(e) Enzyme deficit: The cell line is HGPRT (hypoxanthine-guanine-phosphoribosyl-transferase) deficient cell line and dies in RPMI-1640 culture medium containing $1 \times 10^{-4}$M hypoxanthine, $4 \times 10^{-7}$M aminopterin and $1.6 \times 10^{-5}$M thymidine.

(f) Number of chromosomes: 43-54.

(g) Substance productivity: The cell line has sustained ability to produce a colony-stimulating factor (CSF).

The cell line of the invention is useful for producing a human CSF in large quantities with high purity. The present cell line retains high ability to produce the CSF for a prolonged period of time with good stability. The cell line is HGPRT deficient cell line, is also useful as parental cells for fusion with human T cells and has a distinct cell surface phenotype, which use can be made of favorably in selecting fused cells derived from such cells.

The cell line of the present invention, which is characterized as above, has the cytologic and other properties to be described below in detail.

(1) Morphological characteristics

The AGR-ON cells resemble lymphoid cells, have about two to three times the diameter of normal human peripheral blood T cells and are nearly spherical. The nucleus occupies a large proportion of the cell, and a small amount of protoplasm is observed. The protoplasm includes some granules. Deformed cells may be present occasionally.

(2) Number of chromosomes

The number of chromosomes of "AGR-ON" of the present invention was counted by the following method. A 0.1 μg/ml quantity of demecolcine (trademark "Colcemid", Sigma Chemical Co., Ltd., U.S.A.) was added to a culture of cells in the logarithmic proliferation stage. Two hours later, the suspension of cells was placed into a centrifugal tube and centrifuged at 1000 r.p.m. for 5 minutes. About 1 ml of 1% sodium citrate solution was admixed with the sediment of cells with gentle stirring, and the mixture was allowed to stand at room temperature for about 15 minutes. About 10 ml of a fixing solution (methanol/glacial acetic acid = 3:1) was gently poured onto the mixture, followed by gentle stirring. The mixture was then allowed to stand for 5 minutes and thereafter centrifuged. The cells were suspeneded in a fresh portion of the same fixing solution. After repeating the same procedure 3 times, the cells were suspended in 1 to 2 ml of the fixing solution. The suspension was placed onto a slide in 2 to 3 drops and air-dried. The sample was stained for 15 to 20 minutes with Giemsa solution (Merck & Co., Inc., U.S.A.) diluted to about 2% with 1/15M phosphoric acid buffer (pH 6.8), washed with water and then dried. Well-spread 50 images of AGR-ON cells in the metaphase stage were microscopically observed using a 60× lens to count up the chromosomes.

Table 1 shows the result, which indicates that the number of chromosomes of the present cells ranges from 43 to 54 and is 45 on the average.

TABLE 1

| Number of chromosomes | 43 | 44 | 45 | 46 | 54 |
| --- | --- | --- | --- | --- | --- |
| Number of cells | 5 | 4 | 37 | 3 | 1 |

(3) Expression of T cell specific antigen

"AGR-ON" of the invention was checked for cell surface phenotype in comparison with the known human T leukemic cell lines CCRF-CEM (ATCC No. CCL119) and CEM-AG ® (ACCC No. CRL-8081; Proc. Natl. Acd. Sci., U.S.A., Vol. 78, No. 12, pp. 7717-7721 (1981)) and with human peripheral blood T cells.

A suspension of cells of each type, adjusted to a concentration of $5 \times 10^5$ cells/ml, was reacted with 100 μl of suitable monoclonal antibodies [(Orthomune OKT series monoclonal antibody (Ortho Pharmaceutical Co., Raritan, N.J., U.S.A.) and Becton-Dickinson Leu series monoclonal antibody (Becton & Dickinson, Sunnyvale, Calif., U.S.A.)] at 4° C. for 30 minutes. The cells were then washed twice with minimum essential Eagle's medium (MEM) containing 5% FCS, reacted with FITC (fluorescein isothiocyanate)-conjugated rabbit anti-mouse immunoglobulin (Miles-Yeda Ltd., Israel) and examined for the expression of T cell specific antigen by indirect immunofluorescence. Table 2 shows the result obtained by checking 100 cells, revealing that "AGR-ON" of the invention is 100% positive for Leu 1 and Leu 3a antibodies and is negative for T3, T8 and Leu 2a antibodies.

The Leu 1-positive expression indicates that the present cells are a T cell line, and the T4- and Leu 3a-positive expression shows that they belong to human inducer/helper T lymphocyte subclass.

TABLE 2

| | T cell antigen (%) | | | | | |
|---|---|---|---|---|---|---|
| | T3 | T4 | T8 | Leu 1 | Leu 2a | Leu 3a |
| CCRF-CEM (CCL119) | 9 | 94 | 34 | 97 | 55 | 96 |
| CEM-AG ® (CRL8081) | 42 | 100 | 0 | 100 | 0 | 100 |
| AGR-ON | 0 | 100 | 0 | 100 | 0 | 100 |
| Human peripheral blood T cell | — | — | 36 | — | 42 | — |

(4) Rosette formation

Two hundred AGR-ON cells were checked microscopically at 400× for Rosette formation with EAC (sheep erythrocyte (E) treated with anti-erythrocyte antibody (A) and human complement (C)). Up to 1% of the cells were found positive.

(5) Expression of B cell and macropharge marker (a) Surface immunoglobulin (Ig) was analyzed with use of FITC-conjugated mouse anti-human immunoglobulin (Behring Werke AG, Marburg) by direct immunofluorescence. Up to 1% of the cells were positive.

(b) Human HLA-DR antigen (hereinafter referred to as "DR") was analyzed with use of a monoclonal anti-DR antibody (Becton-Dickinson Co.) by indirect immunofluorescence. Up to 1% of the cells analyzed were positive.

(c) Expression of human B cell specific antigen (B antigen) was analyzed by indirect immunofluorescence with use of a monoclonal anti-human B cell antibody (see Miki, Y. et al., Journal of Immunology, 129, 1921 (1982)) obtained from a hybrid cell line prepared from myeloma P3U$_1$ (provided by Elbert Einstein College of Medicine) and mouse spleen cells immunized with a human B cell line (CESS, provided by Dr. Peter Ralph of Sloan-Kettering Institute for Cancer Research, New York, U.S.A.) transformed with a virus (Epstein-Barr virus). Up to 1% of the cells were positive. The antibody reacts with B cells or the lines thereof but does not react with T cells or the lines thereof.

(d) A BALB/c mouse was immunized with cells of human macrophage tumor cell line U937 to obtain spleen B cells, which were fused with myeloma P3U$_1$ with use of polyethylene glycol to prepare mouse B hybridoma which produces a monoclonal antibody against human macrophages (see Maruyama S. et al., Journal of Clinical Immunology, 3, 57 (1983)). Although the antibody specifically combines with U937 and normal human macrophages, the antibody does not react with normal human T cells or B cells, nor with human T cell line or human B cell line. The expression of human macrophage antigen was analyzed with use of the antibody by indirect immunofluorescence. Up to 1% of the cells were positive.

(6) Proliferation

The AGR-ON cells proliferate satisfactorily in RPMI 1640 culture medium (Flow Laboratories, U.S.A.) containing 8-azaguanine (8-AG, 100 μM), 10% FCS, 100 μg/ml streptomycin, 100 units/ml penicillin G, 50 μg/ml gentamycin, $5 \times 10^{-5}$M 2-mercaptoethanol and 1 mM glutamine.

(7) Proliferation conditions

The AGR-ON cells generally proliferate satisfactorily at a temperature of 36° to 38° C. and pH of 7.2 to 7.3. It is suitable to use an incubator containing 5% carbon dioxide and 95% air.

(8) Subculture

The AGR-ON cells can be subcultured continuously and indefinitely.

(9) Preservation in frozen form

The AGR-ON cells can be preserved easily for a prolonged period of time in a mixture of 10% dimethyl sulfoxide (DMSO) and 90% of RPMI-1640 culture medium containing 20% FCS, as frozen in liquid nitrogen. (10) Resistance to 8-azaguanine (8-AG)

The AGR-ON cells are resistant to 8-azaguanine (100 μM) and die in a medium (HAT medium) containing $1 \times 10^{-4}$M hypoxanthine, $4 \times 10^{-7}$M aminopterin and $1.6 \times 10^{-5}$ thymidine. This indicates that "AGR-ON" is deficient in hypoxanthine-guanine-phosphoribosyl-transferase (HGPRT).

(11) Mitogen responsiveness

When 10 to 100 μg/ml of concanavalin A (Con A) and 1 to 10% of plant lectin, phytohemagglutinin (PHA) are added to the medium, the proliferation of the AGR-ON cell line is inhibited to some extent. Pokeweed mitogen (PWM), as well as protein A (Pro A), produces no influence on the proliferation of the line at any concentration whatever.

(12) Capability of producing substances other than CSF

The present cells are capable of continuously producing burst promoting activity (BPA) as assayed in accordance with the method of D. W. Golde et al (Proc. Natl. Acad. Sci., U.S.A., Vol. 77, No. 1, 593–596 (1980)).

The present cells are capable of continuously producing a factor which stimulates immunoglobulin secretion in human blood B lymphocytes as assayed in accordance with the method of Saiki and Ralph, J. Immunol. 127, 1044 (1981).

The present cells are not capable of producing γ-interferon as assayed in the system using FL cells from human amnion (Proc. Soc. Exp. Biol. Med., 94, 532 (1957)) and Sindbis virus in accordance with the method of Sudo et al (Tetsuo Sudo, Reiko Okubo, Masahiko Iizuka and Shigeyasu Kobayashi, The 42nd Symposium on Virus-inhibiting Factors, 1982), and also are not capable of producing interleukin-2 as assayed according to the method of Watson et al (J. Exp. Med., 150, 849 (1979)).

The cell line of the invention, "AGR-ON", thus characterized can be obtained from 8-AG resistant human T leukemic cells by cloning in usual manner. Such 8-AG resistant human T leukemic cells are prepared by a usual method, for example, by the method disclosed in Published Unexamined Japanese Patent Application (Kokai) 206383/1982, from known human T leukemic cells, e.g., CCRF-CEM (J. Kaplan et al., Exp. Med., 139, 1070–1076 (1974)), by culturing such cells in RPMI 1640 medium containing 10% FCS and 8-azaguanine (8-AG) and then successively transferring these cells to such media with increased concentrations of 8-AG. Stated more specifically, the cells are cultured in this type of medium containing, for example, 2 $\mu$M of 8-AG for 1 week first, then in the same medium containing 16 $\mu$M of 8-AG for 1 week and thereafter similarly in media with the concentration of 8-AG increased 2-fold in succession. Finally an 8-AG resistant cell line is obtained alive in a medium containing 100 $\mu$M of 8-AG. Typical of such 8-AG resistant cell lines is, for example, the aforementioned CEM-AG ® (ATCC No. CRL-8081).

Cloning of "AGR-ON" is conducted by a usual method, for example, the soft agar method (Methods in Enzymology, Vol., 73, pp. 1–45 (1981)). With this method, a cell suspension diluted to 200 to 2000 cells/ml is prepared with use of a culture medium (e.g. RPMI 1640 containing 8-AG) of two-fold concentration. A quantity of the suspension is immediately mixed with an equal amount of 0.3% solution of soft agar (Difco Lab., Detroit. MI.), and the mixture is plated in a plastic dish. The amount of the mixture, which varies with the size of the dish, is 1 to 1.5 ml for a dish of 3 cm in diameter or 2 to 2.5 ml for a dish of 5 to 6 cm in diameter. In 10 to 14 days after the start of incubation, colonies are formed which can be observed with the unaided eye. At this time, each of the colonies are picked up under inverted microscope using a Pasteur pipette and placed into a culture medium in incubation plate(s) having a flat bottom with 96 wells.

The colonies obtained are checked for CSF productivity by a usual method (e.g., Journal of Immunological Methods, 42, pp. 253–284 (1981)) to isolate "AGR-ON" as a single cell line.

The cell line of the invention, "AGR-ON", thus obtained has the foregoing characteristics. The cell line was deposited at the Amercian Type Culture Collection (ATCC), 12301 Parklawn Drive, Rockville, Md. 20852, U.S.A. on Jan. 24, 1983 and has been assigned "ATCC No. CRL-8199".

CSF is prepared from the present cell line "AGR-ON" by incubating the cell line by the usual method of tissue culture and separating the factor from the supernatant of the culture.

The cell line is incubated in a usual nutrient culture medium, which is not limited particularly. Examples of useful culture media are prepared from those generally used for such purposes, e.g., RPMI-1640, MEM (minimum essential Eagle's media), etc., by modifying them with FCS. The incubating conditions are not limited particularly, either; for example, the cell line is incubated at a concentration of 1–10 $\times 10^5$ cells/ml under the foregoing conditions of proliferation usually for about 3 days. The resulting culture medium contains CSF, which is separated off and further purified by salting out, chromatography, electrophoresis, dialysis or like physicochemical method.

The present cell line "AGR-ON" affords the desired CSF very easily in a high yield with high purity. The present invention assures mass production of the CSF on a commercial scale. Mmreover, the CSF thus obtained has high activity and low toxicity, remains free of degradation in its activity during the production process and is advantageously usable for the same applications as the known CSFs.

The present invention will be described in greater detail with reference to the following examples and test examples.

EXAMPLE 1

Preparation of "AGR-ON"

CEM-AG ® (ATCC No. CRL-8081) was diluted with the same culture medium containing 100 $\mu$M 8-AG to a concentration of 1000 cells/ml to obtain a cell suspension, which was immediately mixed with 0.3% solution of soft agar (Difco Lab.) heated to 37° C. The mixture was plated in plastic dishes (3 cm in diameter) in an amount of about 1 ml in each dish. In 14 days after the start of incubation, each of the colonies formed were picked up with a Pasteur pipette under inverted microscope and placed into the same culture medium as above in an incubation plate having a flat bottom with 96 wells, where the colonies were further incubated. Each of the supernatants were checked for CSF activity as stated in the test example below, giving the cell line of the invention, "AGR-ON". The cell line thereafter exhibited brisk proliferation in RPMI-1640 culture medium containing 100 $\mu$M of 8-AG and 10% FCS. The cell line has since been subcultured in the same kind of medium. The cell line had the cytologic and other characteristics already stated.

TEST EXAMPLE 1

(1) The cell line "AGR-ON" obtained in Example 1 was adjusted to a concentration of $5 \times 10^5$ cells/ml with RPMI-1640 medium containing 10% FCS and was incubated in a plastic flask (25 cm$^2$/70 ml, Corning Glass Works; Corning, N.Y., U.S.A.) at 37° C. for 3 days in a 5% carbon dioxide gas incubator. A 10 ml quantity of the supernatant of the culture obtained by centrifuging was treated with 80% saturated ammonium sulfate. The precipitate was collected by centrifuging and dissolved in 1 ml of physiological saline. The solution (AGR-ON sample) was tested as described below.

(2) CSF activity

The AGR-ON sample was tested for CSF activity according to the method of Ian et al (J. Immunol. 128, p. 168 (1982)), using the following culture media.

\* Culture medium I (MEM medium of 2-fold concentration)

| | |
|---|---|
| MEM powder (Flow laboratories Inc., U.S.A.) | 2.68 g |
| Sodium bicarbonate aqueous solution (7 w/v %) (Trademark "Meylon", product of Otsuka Pharmaceutical Co., Ltd., Japan) | 10.6 ml |
| Penicilline G | 20000 units |
| Streptomycin | 20 mg |
| Gentamycin | 10 mg |
| 2-Mercaptoethanol | $5 \times 10^{-5}$ M |
| Distilled water | q.s. 100 ml |

\* Culture medium II (MEM medium)

| | |
|---|---|
| MEM powder | 13.4 g |
| Sodium bicarbonate aqueous solution (7 w/v %) (Trademark "Meylon", product of Otsuka Pharmaceutical Co., Ltd., Japan) | 52.9 ml |
| Penicillin G | 100000 units |
| Streptomycin | 100 mg |
| Gentamycin | 50 mg |
| 2-Mercaptoethanol | $5 \times 10^{-5}$ M |
| Distilled water | q.s. 1000 ml |

\* Culture medium III

| | |
|---|---|
| Culture medium I | 30 ml |
| Culture medium II | 20 ml |
| FCS (Irvine Scientific, U.S.A.) | 20 ml |

Agar (1%, Difco Lab.) was melted in an autoclave and maintained at 43° C. 10 ml quantity of the solution was admixed with 23.3 ml of the culture medium III maintained at 37° C., and the mixture was maintained at 37° C.

Bone marrow cells (BMC) collected from the femur of a BALB/c mouse were washed with Hank's balanced salt solution twice and adjusted to a concentration of $10^7$ cells/ml with the medium II. A 1 ml quantity of the suspension was admixed with the agar culture medium, and the mixture was maintained at 37° C. ($2.9 \times 10^5$ cells/ml). A 1 ml quantity of the mixture was quickly admixed with each of 0.1 ml diluted portions of the AGR-ON sample having stepwise varying conentrations, and the mixture was allowed to stand at room temperature until the medium solidified. The mixture was then placed into a carbon dioxide gas incubator at 37° C. to start incubation. The colonies formed in 10 days after the start of incubation were counted up. FIG. 1 shows the result. In the diagram, the final dilution of the sample is plotted as abscissa v. CSF activity, i.e., the number of colonies per plate (C/P) as ordinate. The flexed lines shown represent the following.

●—●: AGR-ON sample.

■—■: Sample prepared from human splenocytes. (An authentic sample obtained by preparing a suspension of cells from the spleen provided by a patient who received splenolaparotomy, adjusting the suspension to a concentration of $1 \times 10^6$ cells/ml with RPMI-1640 medium containing 1% FCS, stimulating the cells with 0.1% PHA-P (Difco Lab.) for 2 days and separating the supernatant by centrifugation, followed by the same procedure as in the foregoing para. (1).)

▲—▲: Sample prepared from human peripheral blood mononuclear cells. (An authentic sample obtained by separating purified mononuclear cells from the peripheral blood of a healthy person on a Ficoll-Isopaque density gradient centrifugation (Pharmacia Fine Chemicals, Sweden; δ=1.078 g/cm³), preparing a suspension of $1 \times 10^6$ cells/ml using the mononuclear cells and RPMI-1640 medium containing 1% FCS, stimulating the cells with 0.1% PHA-P for 2 days, and separating the supernatant by centrifugation, followed by the same procedure as in the foregoing para. (1).)

FIG. 1 demonstrates that the culture supernatant of the AGR-ON has CSF activity. The colonies examined were morphologically found to be granulocytes and macrophages.

(3) Comparison with parental cells

A comparative sample was prepared in the same manner as above using CCRF-CEM (ATCC No. CCL119). AGR-ON sample was also obtained by the same method as in para. (1). In the same manner as in para. (2), 0.2 ml portions of the comparative sample and AGR-ON sample were tested for CSF activity.

Table 3 below shows the result.

TABLE 3

| Cell line | count of colonies/plate |
|---|---|
| AGR-ON | 307 |
| CCRF-CEM | 0 |

(4) Gel filtration

Each of the samples in para. (2) was fractionated with a column of Ultrogel AcA 54 (2.2×90 cm, LKB, Bromma, Sweden). The column was brought to an equilibrium with 0.5M NaCl, 0.01M sodium phosphate buffer and 0.05% polyethylene glycol 6000 before fractionation. The sample was passed through the column at a flow rate of 19 ml/hr to give 2 ml fractions. Separation of proteins was monitored by measuring the absorbance at 280 mμ. The CSF activity of the fractions was measured by the above method.

Figure 2:
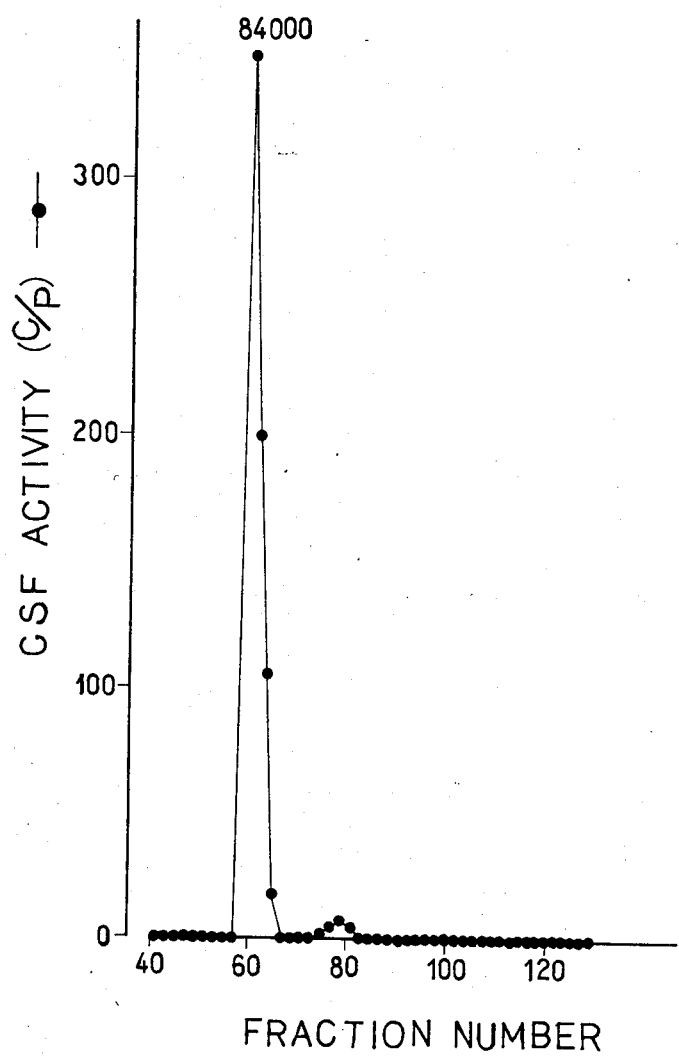
Figure 3:
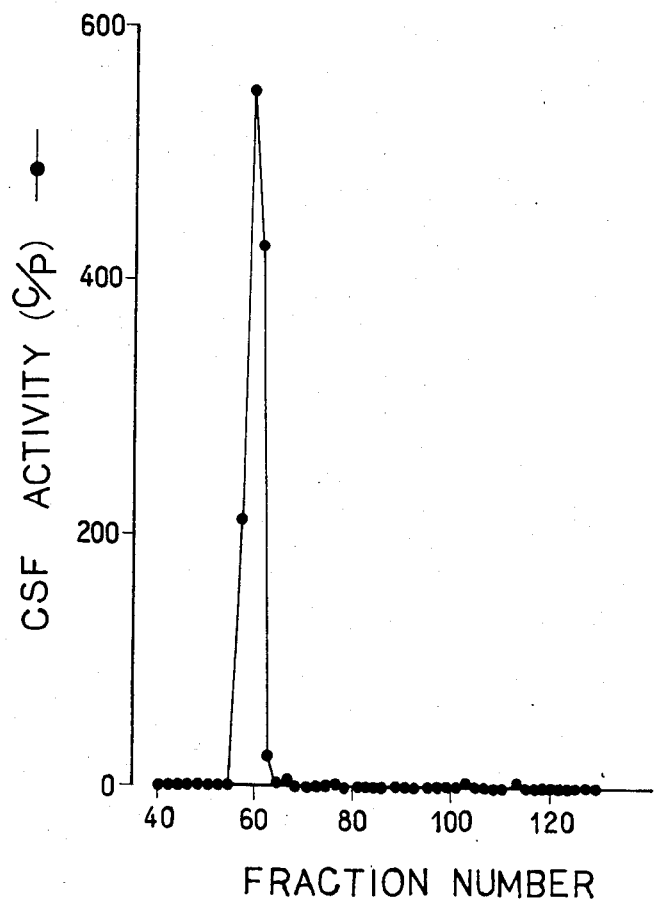
Figure 4:
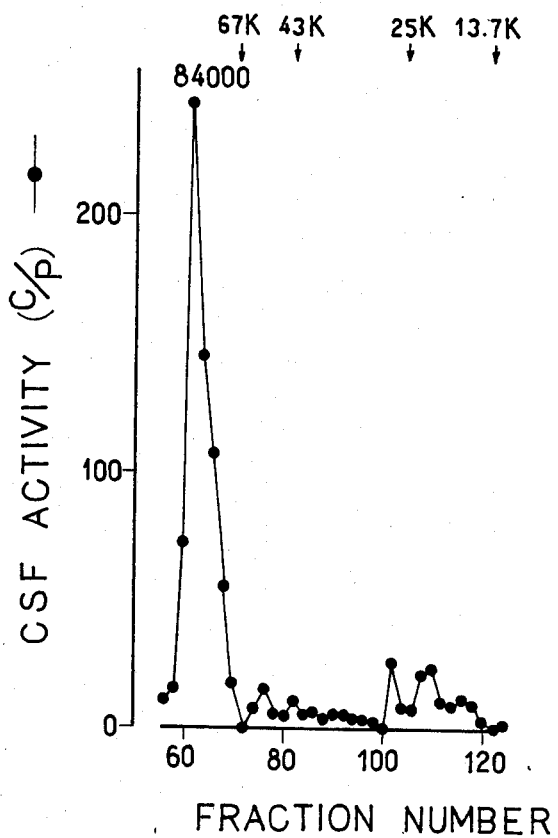

The results are given in FIGS. 2 to 4 which show the elution patterns determined by the gel filtration of the samples.

In these drawings, the CSF activity (count of colonies/plate, abbreviated as "C/P") is plotted as ordinate vs. the fraction number as abscissa. The AGR-ON sample was represented in FIG. 2, the sample prepared from human peripheral blood mononuclear cells in FIG. 3, and the sample prepared from human splenocytes in FIG. 4.

Estimated from a standard-molecular-weight kit (Pharmacia Fine Chemicals, Sweden), the CSF from AGR-ON has a molecular weight of about 84,000, which nearly matches those of CSFs from human peripheral blood mononuclear cells and human splenocytes.

(5) The CSF assay of the AGR-ON sample obtained in para. (1) was conducted in the same manner as in para. (2) except that human BMC was used in place of mouse BMC (see Blood, 60; 595 (1982)).

Used as a positive control was a conditioned medium (hereinafter referred to as "5637 CM") similarly prepared from human bladder carcinoma line 5637 (Cell. Immunol., 71; 215 (1982)).

Table 4 shows the result.

TABLE 4

| Stimulant | Colonies/$10^5$ BMC cells |
|---|---|
| None | 13 ± 2 |
| 5637 CM | 181 ± 29 |
| AGR-ON sample | 683 ± 14 |

The colonies obtained by the addition of the AGR-ON sample were microclusters of less than 50 cells per colony and containing granulocytes and macrophages.

The above assay was repeated with an incubation period of 2 weeks, and the activity of the mixed colony-CSF was examined.

Table 5 shows the results

TABLE 5

| Stimulant | Colonies/$10^5$ BMC cells |
| --- | --- |
| None | 0 |
| AGR-ON sample | 2.3 ± 0.3 |

The colonies obtained included erythrocytes, granulocytes, macrophages and megakaryocytes.

TEXT EXAMPLE 2

(1) The AGR-ON obtained in Example 1 was adjusted to a concentration of $2 \times 10^6$ cells/ml with use of RPMI-1640 culture medium containing 20 mM of N-2-hydroxyethylpiperazine-N'-2-ethanesulfonic acid (hereinafter referred to as "HEPES") and was incubated in a cell incubating flask (working vol, 2000 ml, Shibata-Hario Co., Ltd.) at 37° C. for 4 days. About 2000 ml of the supernatant centrifugally obtained from the culture was subjected to ultrafiltration first with pellicon casset system (Millipore Corp., Bedford, Mass., U.S.A.) and then with ultrafiltration cell model 8400 through YM-5 membrane (Amicon Corp., Lexington, Mass., U.S.A.). The concentrate thus obtained was then dialyzed against $PBS^-$ containing 0.005% PEG (pH=7.2, hereinafter referred to as "PEG-PBS", in which "PBS" stands for phosphate buffered saline), giving 21.5 ml of concentrate containing 6.34 mg protein/ml.

When examined in the same manner as in Test Example 1-(2), the concentrate was found to have CSF activity of 26,400 Units/ml, wherein 1 Unit refers to the activity to form 1 colony per plate. ("Unit" will be represented by "U" hereinafter.)

Figure 5:
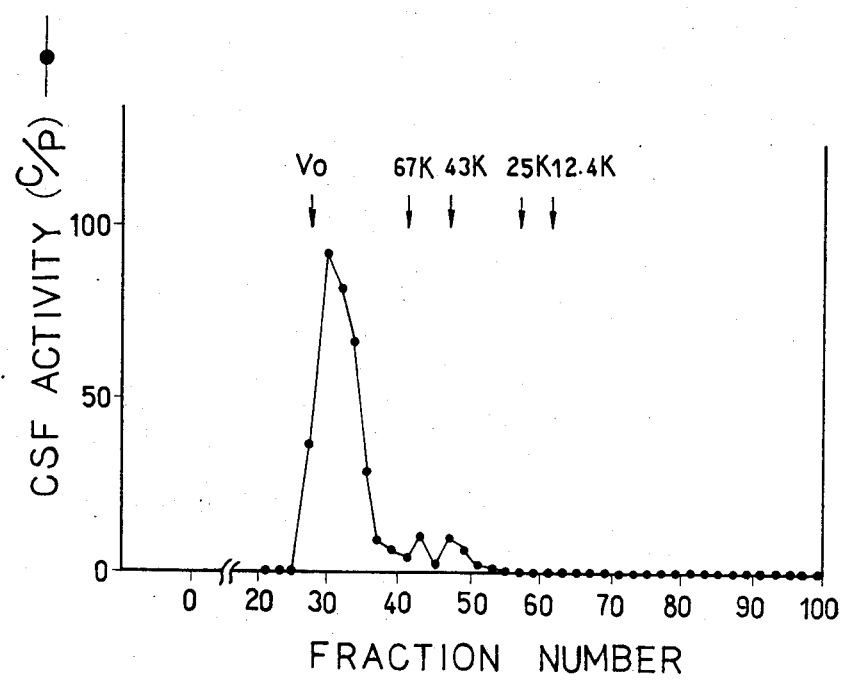

(2) A column packed with Ultrogel AcA44 (LKB, Bromma, Sweden) and measuring 2.2 cm in diameter and 86 cm in length was first brought to an equilibrium with PEG-PBS and then charged with 4 ml of the concentrate obtained by the above procedure (1), followed by elution with PEG-PBS (flow rate 16.2 ml/hr., 4.2 ml/fraction). FIG. 5 shows the elution pattern.

In the following experiments, the CSF activity was determined in the same manner as in Test Example 1-(2). The following proteins were used as standard proteins.

Standard A 290,000 Delton (290 K): Glutamate dehydrogenase
142 K: Lactate dehydrogenase
67 K: Enolase
32 K: Adenylate kinase
12.4 K: Cytochrome C The above standard proteins are all products of Oriental Yeast Co., Ltd., Japan.

Standard B

669 K: Thyroglobulin
440 K: Ferritin
232 K: Catalase
158 K: Aldolase
67 K: BSA (bovine serum albumin)
43 K: Ovalbumin
25 K: Chymotrypsinogen
12.4 K: Cytochrome C The above standard proteins are products of Sigma Chemical Co., Ltd., U.S.A.

Vo: Blue-Dextrane 2000 (Pharmacia Fine Chemicals)

FIG. 5 shows that the main activity was found in the fractions of 100 K and above.

(3) The concentrate obtained by the same procedure as (1) (8.09 mg protein/ml; 67,400 U/ml) was subjected to preparative high performance liquid chromatography (HPLC) under the following conditions.

Column: TSK GEL 4000SWG (21.51 mm (diameter)×600 mm, Toyo Soda Co., Ltd., Japan) equipped with TSK guard column SWG (21.51 mm (diameter)×75 mm).
Eluent: PEG-PBS.
Injected vol.: 4 ml.
Flow rate: 3 ml/min.
Fraction: 3 ml/fraction.

Figure 6:
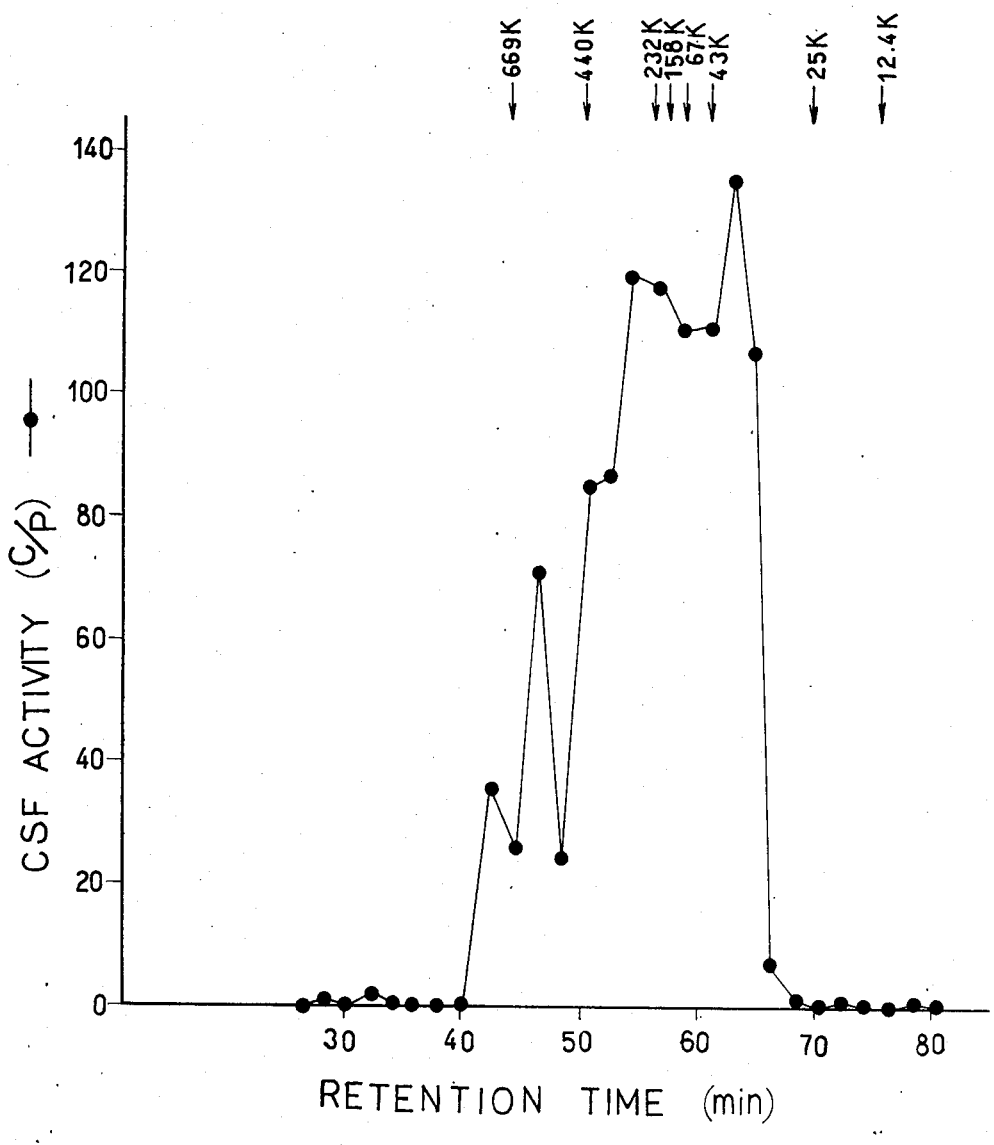

FIG. 6 shows the result. The main CSF activity was observed around 37 K and about 320 K, while minor activity was observed around 600 K and around 700 K.

(4) (a) The fraction (250 ml, 0.176 mg protein/ml) obtained with a retention time of 48 to 67 minutes in the above procedure (3) was passed through Con A column under the following conditions.

Column: Con A-Sepharose (Pharmacia Fine Chemicals) column (1.6 cm (diameter)×15.5 cm).
Eluent: PEG-PBS and PEG-PBS containing 0.1M α-methyl-mannoside (hereinafrer referred to as "MM-PBS").
Flow rate: 31.5 ml/hr.
Fraction: 10.5 ml/fraction.

Figure 7:
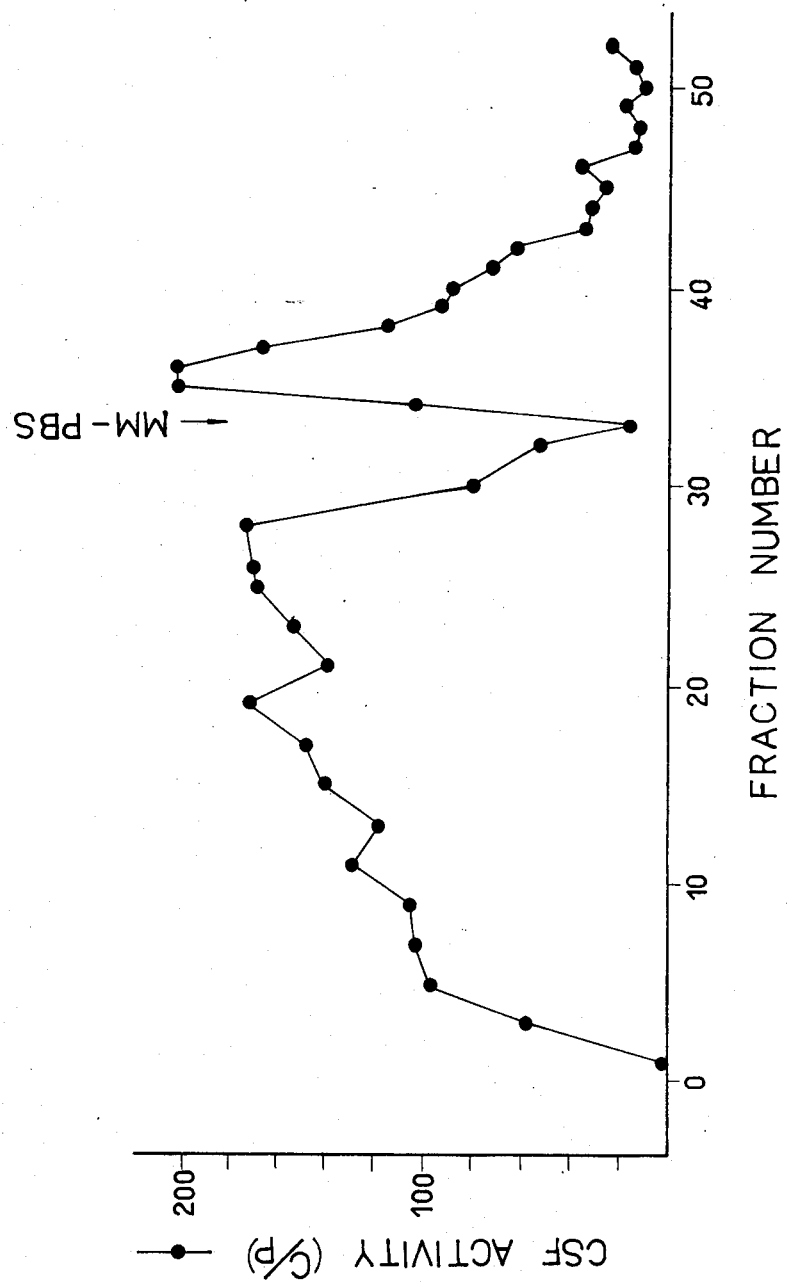

FIG. 7 shows the result.

(4) (b) A 313 ml quantity of the fractions (0.342 mg protein/ml; 2347 U/ml) with Fraction Numbers 2 to 33 obtained in the above procedure (a) were subjected to chromatography again under the following conditions.

Column: Con A-Sepharose column (1.6 cm (diameter)×35 cm).
Eluent: PEG-PBS and MM-PBS.
Flow rate: 17.6 ml/hr.
Fraction: 10.3 ml/fraction.

Figure 8:
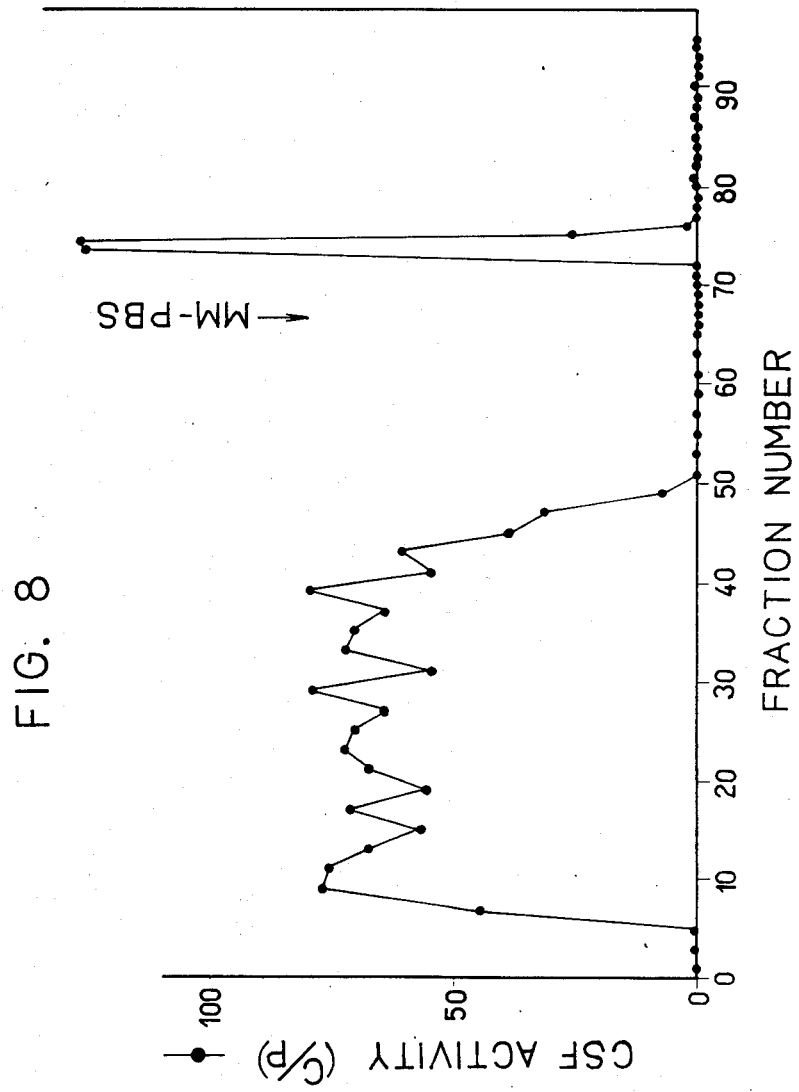

FIG. 8 shows the result.

FIGS. 7 and 8 indicate that the CSF from AGR-ON includes two kinds; one having affinity for Con A, and the other having no affinity therefor.

(5) The same procedure as the foregoing (1) was repeated except that the concentrate resulting from ultrafiltration with pellicon casset system was dialized against 0.02M sodium phosphate buffer containing 0.005% PEG (pH=7.4, hereinafter referred to as "NaPB") to obtain a concentrate (0.677 mg protein/ml, 2480 U/ml). The concentrate was passed through DEAE-Sepharose CL-6B (Pharmacia Fine Chemicals) column (1 cm (diameter)×14.5 cm) already equilibrated with NaPB, washed with NaPB and then subjected to linear gradient elution with to 1M NaCl (flow rate 1 ml/min, 10 ml/pass through fraction, 5 ml/eluate fraction).

Figure 9:
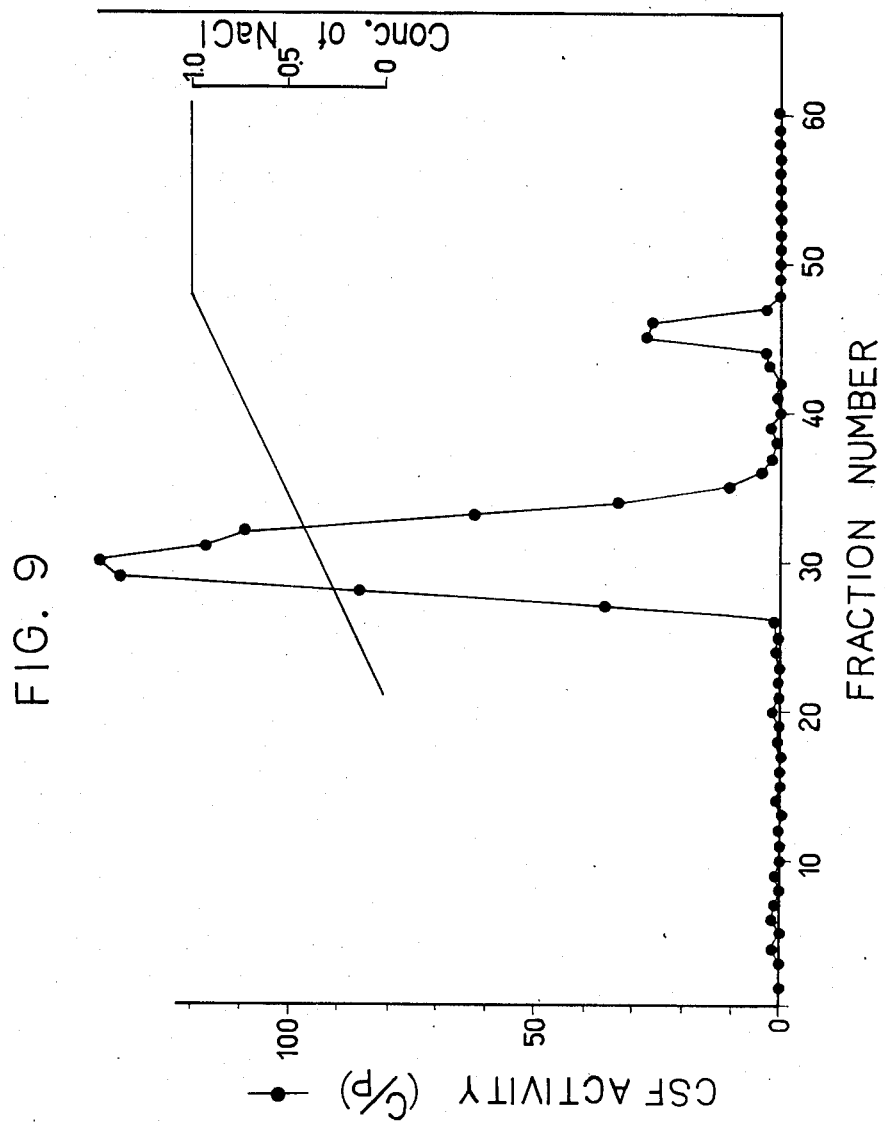

FIG. 9 shows the result.

The fractions in the NaCl concentration range of 0.2 to 0.5M were found to exhibit main CSF activity. Minor activity was observed in the fraction in the NaCl concentration range of 0.9 to 1.0M.

(6) To 28 ml of the fractions with Fraction Number 27 to 34 (0.523 mg protein/ml, 3240 U/ml) obtained in the above procedure (5) was added ammonium sulfate to a final concentration of 1M, and the mixture was stirred at 4° C. for 2 hours and then subjected to chromatography under the following conditions.

Column: Phenyl-Sepharose CL-4B (Pharmacia Fine Chemicals) column (1 cm (diameter)×6.4 cm).

Eluent:
(1) Linear gradient elution from 1M $(NH_4)_2SO_4$-0.01M sodium phosphate buffer (pH=6.8) to 0.01M sodium phosphate buffer (ph=6.8).
(2) Linear gradient elution from 0.01M sodium phosphate buffer to 70 v/v % ethylene glycol (EG)-0.01M sodium phosphate buffer.
(3) 100% EG.

Flow rate: 0.5 ml/min.
Fraction: 3 ml/fraction.

Figure 10:
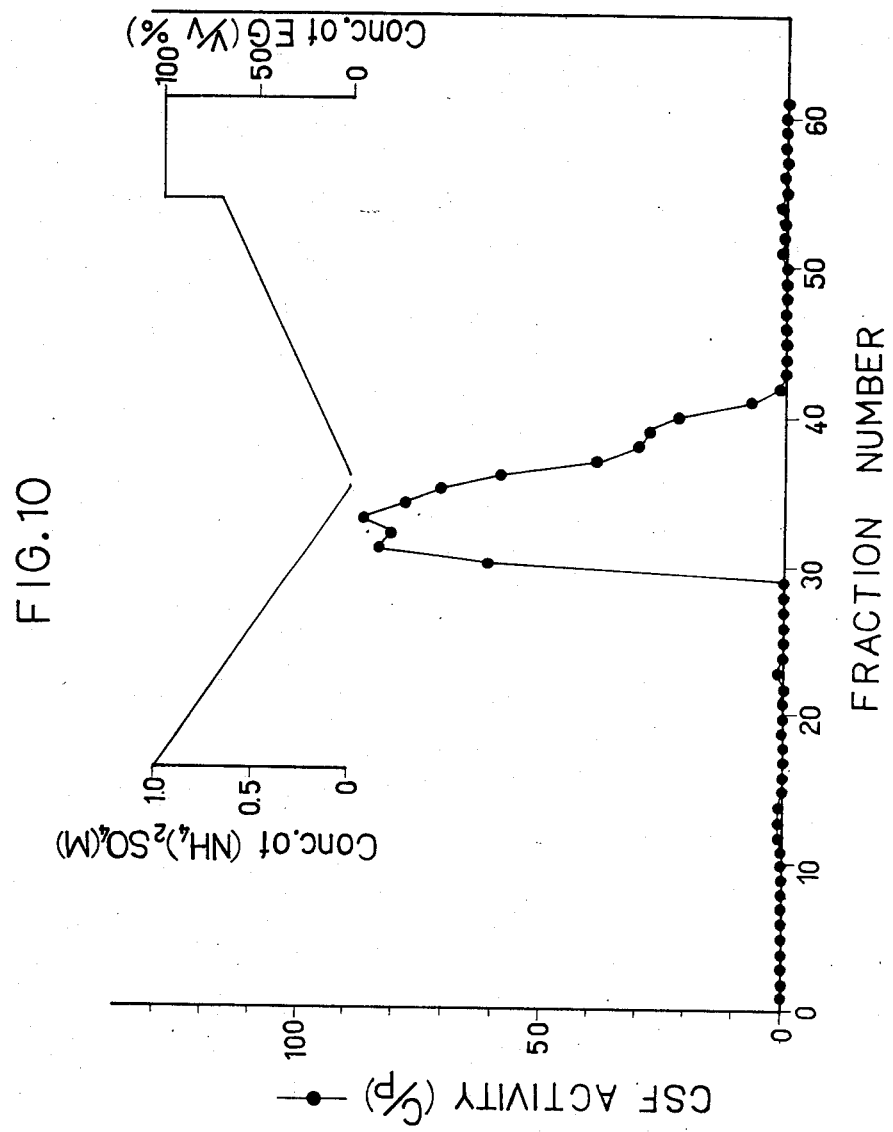

FIG. 10 shows the result. The fraction in the ammonium sulfate concentration range of 0.25 to 0M and in the EG concentration range of 0 to 20 v/v % were found to exhibit CSF activity.

(7) (a) The concentrate obtained by the procedure (1) was subjected to ultrafiltration over YM-5 membrane, and the concentrate was dialyzed against 0.025M imidazole-HCl butfer (pH=7.4), giving a concentrate (11.25 mg protein/ml, 86,800 U/ml), which will hereinafter be referred to as a "normal concentrate".

(7) (b) The procedure (1) was repeated except that 1 μg/ml of tunicamycin (hereinafter referred to as "TM"), an inhibitor of N-glycosylation, was added to the culture medium for incubating AGR-ON to obtain a concentrate (3.418 mg protein/ml, 62,460 U/ml), which will hereinafter be referred to as a "TM-treated concentrate".

(7) (c) The concentrates resulting from the procedures (a) and (b) were subjected to HPLC under the following conditions.
Column: TSK GEL 3000 SW (7.51 mm (diameter)×600 mm) equipped with TSK guard column SW (7.51 mm (diameter)×75 mm).
Eluent: PEG-PBS.
Injected volume: 300 μl.
Flow rate: 0.8 ml/min.
Fraction: 0.8 ml/fraction.

Figure 11:
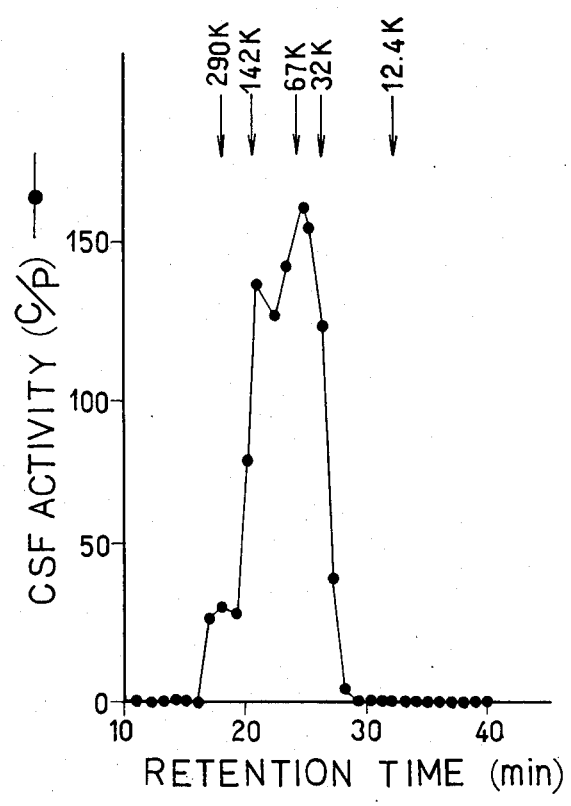
Figure 12:
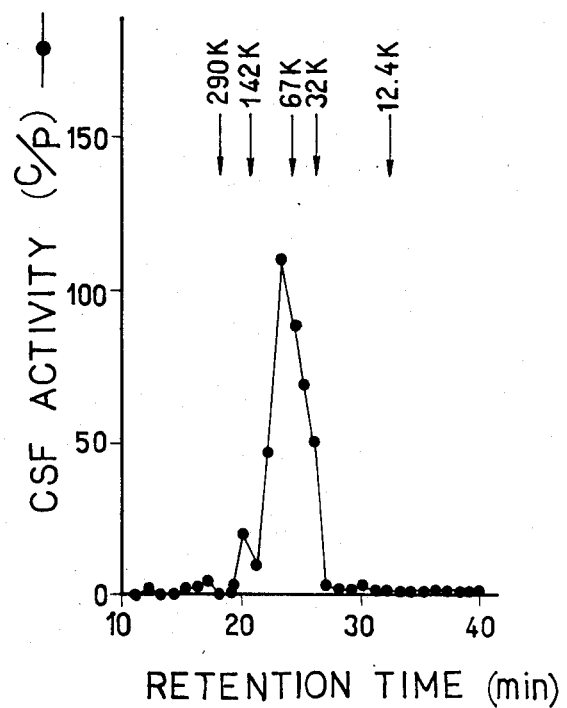

FIG. 11 shows the result achieved with the normal concentrate, and FIG. 12 the result with the TM-treated concentrate.

The main CSF activity resulting from the normal concentrate was observed with the fraction of about 60 K, and the main CSF activity resulting from the TM-treated concentrate was observed with the fraction of about 70 K. Minor CSF activity was observed with the fraction of about 140 K to 290 K only in the case of the normal concentrate. Thus the treatment with TM eliminated the CSF activity from high-molecular-weight fractions presumably because glycosylation of CSF molecule was inhibited in the presence of TM.

(8) A concentrate obtained in the same manner as the procedure (7)-(a) (17.23 mg protein/ml, 6,600 U/ml) and the TM-treated concentrate resulting from the procedure (7)-(b) were subjected to chromatofocusing under the following conditions.
Column: Column (1 cm (diameter)×13.5 cm) of Polybuffer exchangers PBE94 (Pharmacia Fine Chemicals) equilibrated with 0.025M imidazole-HCl buffer (pH=7.4).
Eluent: Eight-fold dilution (pH 7.4) of Polybuffer 74 (Pharmacia Fine Chemicals) and 1M NaCl.
Injected volume: 1.7 ml for the normal concentrate, or 1 ml for the TM-treated concentrate.
Flow rate: 0.5 ml/min.
Fraction: 3 ml/fraction.

Figure 13:
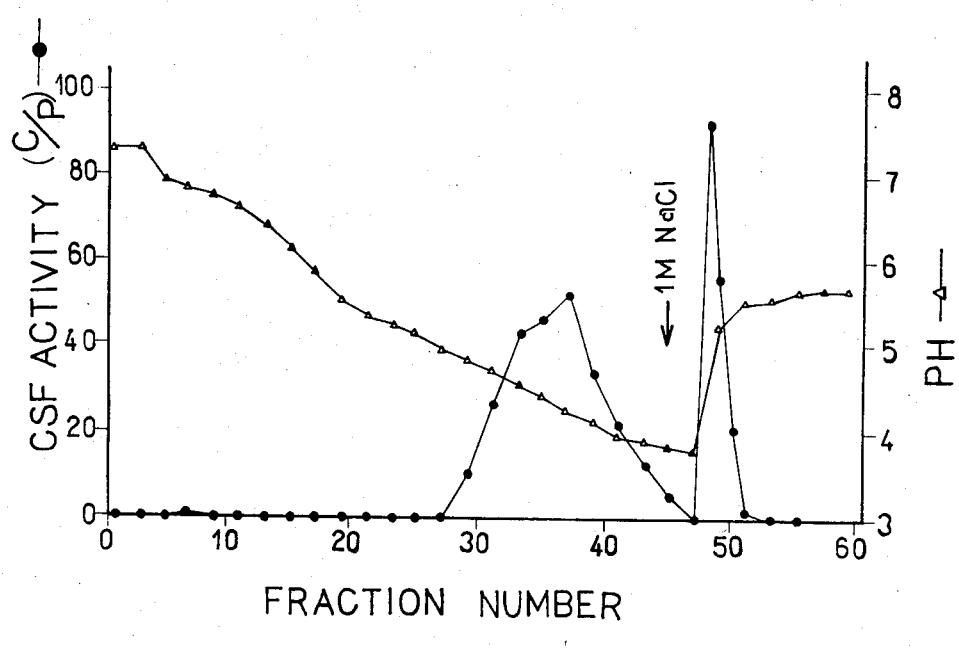
Figure 14:
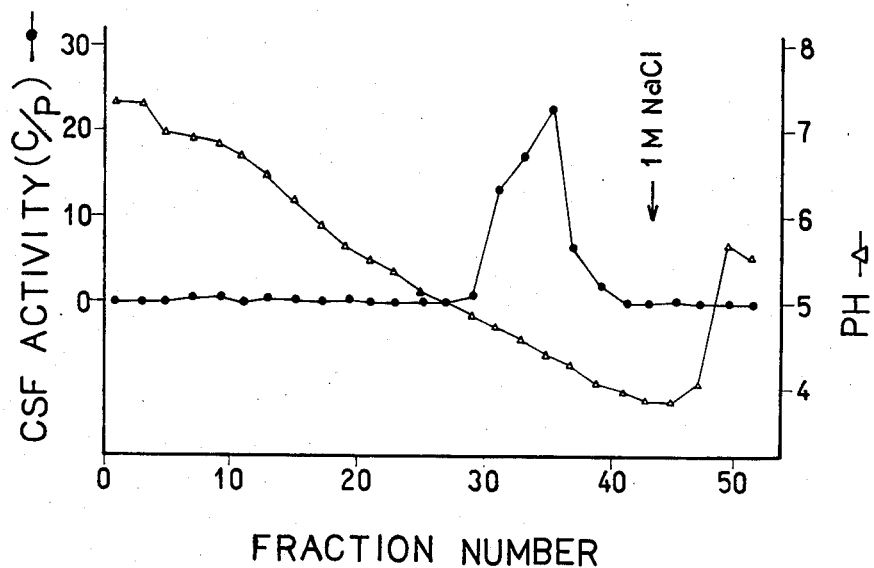

FIG. 13 shows the result achieved with the normal concentrate, and FIG. 14 the result achieved with the TM-treated concentrate. In the absence of TM, the CSF from AGR-ON was observed with the fraction of pI of 3.8 to 4.9 (main peak pI=4.2) and with the fraction eluted with 1M NaCl. The treatment with TM eliminated the CSF activity from the fraction eluted with 1M NaCl. This appears to indicate the presence of sialic acid in a carbohydrate moiety of the CSF of the fraction eluted with 1M NaCl.

(9) HPLC was conducted under the following conditions for the fractions with Fraction Numbers 28 to 45 (2.78 mg protein/ml, 35,500 U/ml) resulting from the chromatofocusing of the normal concentrate by the procedure (8) and for the fractions (1.60 mg protein/ml, 18,100 U/ml) with Fraction Numbers 48 to 51 similarly obtained by the same procedure (8).
Column: TSK GEL 3000 SW (7.51 mm (diameter)×600 mm) equipped with TSK guard column SW (7.51 mm (diameter)×75 mm).
Eluent: PEG-PBS.
Injected volume: 300 μl.
Flow rate: 0.8 ml/min.
Fraction: 0.8 ml/fraction.

Figure 15:
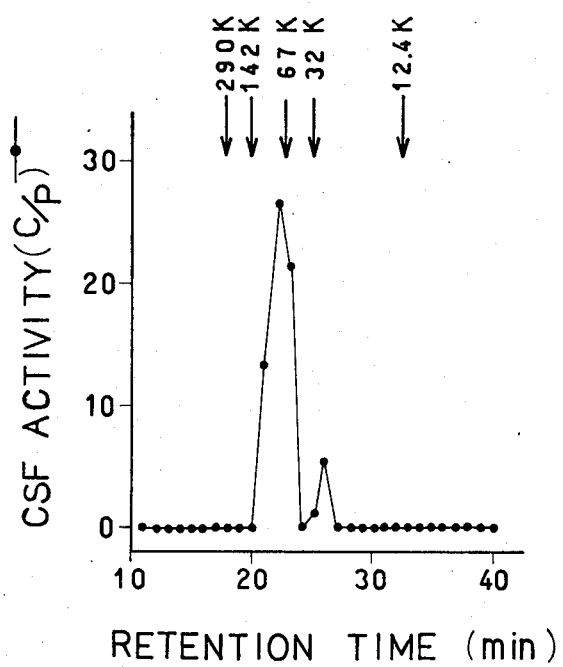
Figure 16:
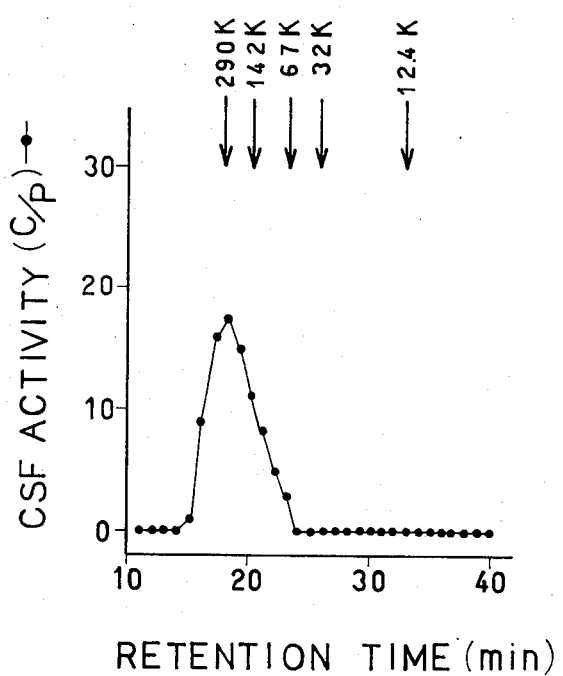

FIG. 15 shows the result achieved by the fractions with Fraction Numbers 28 to 45, and FIG. 16 shows the result obtained by the fractions with Fraction Numbers 48 to 51. CSF with the main peak at pI=4.2 was eluted at about 67 K. 1M NaCl-eluted fractions had a peak around 250 K and were obtained at 67 K and above. These results substantiate the result achieved by the procedure (7) and (8).

(10) Cell growth (a) AGR-ON was adjusted to about $1 \times 10^5$ to $2 \times 10^5$ cells/ml with one of RPMI-1640 media containing various serums, incubated in a cell incubating flask (working vol. 200 ml, NUNC, Inter. Med., Denmark) in a 5% carbon dioxide gas incubator at 37° C. and checked for cell density with the lapse of culture time. The results are given in FIG. 17, in which the lines have the following meanings.

X—X : Addition of 5% FCS (Irvine Scientific)
●—● : Addition of 5% newborn calf serum (NCS, same as above)
O—O : Addition of 2.5% NCS
▲—▲ : Addition of 2.5% FCS , (b) Cell density measurements were obtained in the same manner as the procedure (a) except that the following condition were used.
Medium: RPMI-1640 medium containing 25 mM HEPES and further containing FCS or human serum (HS).
Culture: Spinner culture (Bellco 11, Bellco Glass Inc., U.S.A.).
Agitation: 100 r.p.m.
Temperature: 37° C.

Figure 18:
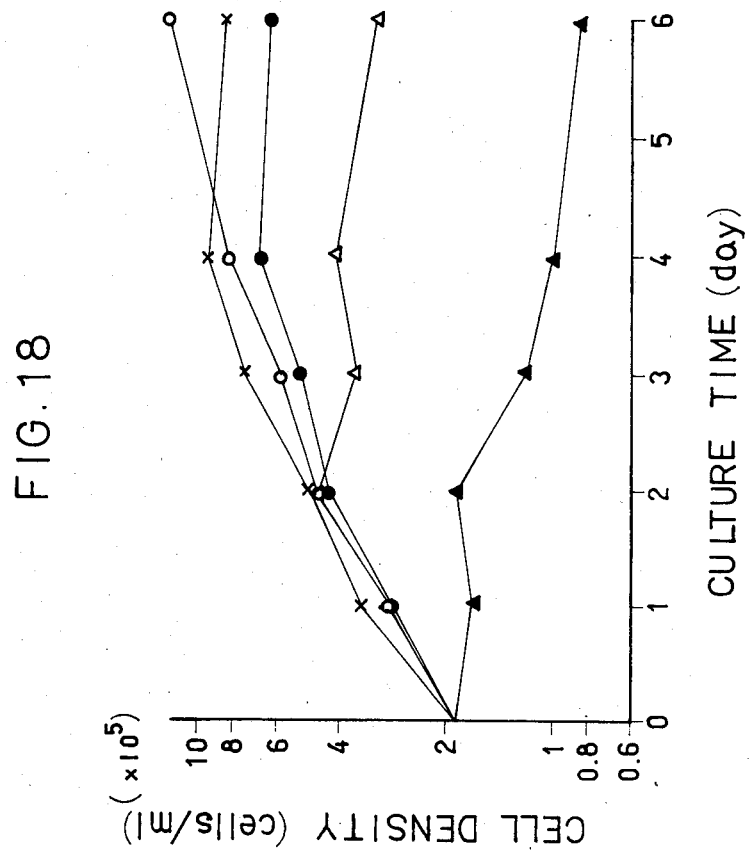

The results are given in FIG. 18, in which the lines have the following meanings.
O—O : Addition of 4% FCS
X—X: Addition of 1% HS
●—● : Addition of 2% FCS
Δ—Δ: Addition of 1% FCS
▲—▲ : Serum-free (control)

Figure 17:
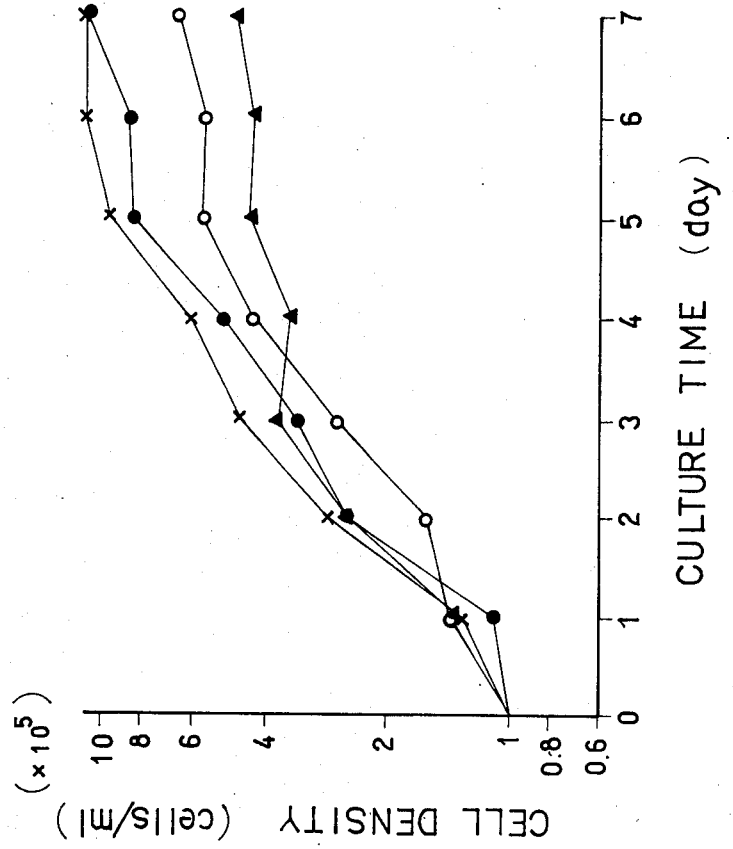

FIGS. 17 and 18 reveal that the proliferation of AGR-ON in vitro requires the presence of serum, and also show that AGR-ON proliferates satisfactorily in the presence of FCS, NCS or HS.

(11) Stability of CSF activity

The concentrate obtained by the procedure (1) was adjusted to the pH values listed in Table 6 with 1N-NaOH or 1N-HCl and tested for stability. Table 6 shows the results.

TABLE 6

| Treatment condition | pH | CSF activity |
|---|---|---|
| 37° C., 3 hr. | 2.5 | Unstable* |
| | 7.5 | Stable |
| | 10 | Stable |
| 56° C., 30 min. | 2.5 | Unstable* |
| | 7.5 | Stable |
| | 10 | Stable |

*About 60% reduction in CSF activity from stable levels.

We claim:

1. A human cultured cell line "AGR-ON" derived from human T leukemic cells and having the following characteristics:
   (a) Form: The cell "ARG-ON" resembles lymphoid cells,
   (b) Proliferation: The cell proliferates satisfactorily in RPMI-1640 culture medium containing 100 M 8-azaguanine (8-AG), 10% fetal calf serum (FCS), $5 \times 10^{-5}$M 2-mercaptoethanol, 100 g/ml streptomycin, 100 units/ml Penicillin G, 50 g/ml gentamycin and 1 mM glutamine,
   (c) Subculture: The cell line can be subcultured continuously and indefinitely,
   (d) Preservation in frozen form: The cell line can be preserved easily in liquid nitrogen for a prolonged period of time,
   (e) Enzyme deficit: The cell line is hypoxanthine-guanine-phosphoribosyl-transferase (HGPRT) deficient cell line and dies in RPMI-1640 culture medium containing $1 \times 10^{-4}$M hypoxanthine, $4 \times 10^{-7}$M aminopterin and $1.6 \times 10^{-5}$M thymidine,
   (f) Number of chromosomes: 43–54,
   (g) Substance productivity: The cell line has sustained ability to produce a colony-stimulating factor and is capable of continuously producing a factor which stimulates immunoglobulin secretion in human blood B lymphocytes, but not capable of producing γ-interferon and also not capable of producing interleukin-2.

2. A human cultured cell line "AGR-ON" as defined in claim 1 which has the identifying characteristics of ATCC Number CRL-8199.

3. A process for preparing the human cultured cell line "AGR-ON" derived from human T leukemic cells as defined in claim 1 comprising cloning human T leukemic cells having resistance to 8-azaguanine and the identifying characteristics of ATCC number CRL-8081 to obtain a cell line having ability to produce a colony-stimulating factor.

4. A process for preparing a colony-stimulating factor comprising incubating in a suitable culture medium the human cultured cell line "AGR-ON" as defined in claim 1 and separating the colony-stimulating factor from the supernantant of the culture.

* * * * *